United States Patent
Choi et al.

(10) Patent No.: US 12,337,049 B2
(45) Date of Patent: *Jun. 24, 2025

(54) METHOD FOR WHITENING SKIN USING COMPOSITION FOR SKIN WHITENING

(71) Applicant: AMOREPACIFIC CORPORATION, Seoul (KR)

(72) Inventors: Eun Jeong Choi, Yongin-si (KR); Young Gyu Kang, Yongin-si (KR); Hyunjung Choi, Yongin-si (KR); Hyoung June Kim, Yongin-si (KR); Wonseok Park, Yongin-si (KR)

(73) Assignee: AMOREPACIFIC CORPORATION, Seoul (KR)

( * ) Notice: Subject to any disclaimer, the term of this patent is extended or adjusted under 35 U.S.C. 154(b) by 0 days.

This patent is subject to a terminal disclaimer.

(21) Appl. No.: 17/746,555

(22) Filed: May 17, 2022

(65) Prior Publication Data
US 2022/0387277 A1    Dec. 8, 2022

(30) Foreign Application Priority Data
May 26, 2021 (KR) .......................... 10-2021-0067754

(51) Int. Cl.
*A61K 8/365* (2006.01)
*A61Q 19/02* (2006.01)

(52) U.S. Cl.
CPC .............. *A61K 8/365* (2013.01); *A61Q 19/02* (2013.01)

(58) Field of Classification Search
None
See application file for complete search history.

(56) References Cited

U.S. PATENT DOCUMENTS

| | | | |
|---|---|---|---|
| 2005/0075398 | A1 | 4/2005 | Banzan et al. |
| 2011/0190389 | A1 | 8/2011 | Arterburn et al. |
| 2014/0079631 | A1 | 3/2014 | Serhan et al. |
| 2015/0126602 | A1 | 5/2015 | Bannenberg et al. |

(Continued)

FOREIGN PATENT DOCUMENTS

| | | |
|---|---|---|
| CN | 102405039 A | 4/2012 |
| CN | 104684389 A | 6/2015 |

(Continued)

OTHER PUBLICATIONS

Maddodi et al., "Shining light on skin pigmentation: the darker and the brighter side of effects of uv radiation," Photochem Photobiol. Sep. 2012: 88 (5):1075-1082. (Year: 2012).*

(Continued)

*Primary Examiner* — Kyung S Chang
(74) *Attorney, Agent, or Firm* — Sughrue Mion, PLLC

(57) ABSTRACT

Provided is a method for whitening a skin of a subject administrating a whitening composition that includes a compound including a structural unit represented by Chemical Formula A and including at least one hydroxyl group and at least one carboxyl group as an active ingredient, to the subject.

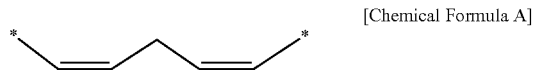

[Chemical Formula A]

In Chemical Formula 1, each substituent is as defined in the specification.

3 Claims, 12 Drawing Sheets

(56) References Cited

U.S. PATENT DOCUMENTS

| | | |
|---|---|---|
| 2015/0165048 A1 | 6/2015 | Mitra et al. |
| 2016/0263019 A1 | 9/2016 | Pernodet et al. |
| 2018/0071190 A1 | 3/2018 | Albrecht et al. |
| 2018/0271818 A1 | 9/2018 | Bannenberg et al. |

FOREIGN PATENT DOCUMENTS

| | | | |
|---|---|---|---|
| EP | 4071241 A1 * | 10/2022 | |
| JP | 4-211004 A | 8/1992 | |
| JP | 2005-502692 A | 1/2005 | |
| JP | 2010-519311 A | 6/2010 | |
| JP | 2015-522535 A | 8/2015 | |
| JP | 2016-505013 A | 2/2016 | |
| JP | 2016-525116 A | 8/2016 | |
| JP | 2017-141204 A | 8/2017 | |
| JP | 2018-509412 A | 4/2018 | |
| JP | 2018-513158 A | 5/2018 | |
| KR | 10-2007-0090928 A | 9/2007 | |
| KR | 10-2017-0122808 A | 11/2017 | |
| KR | 10-2017-0134747 A | 12/2017 | |
| KR | 1020180016341 A | 2/2018 | |
| KR | 10-2018-0096158 A | 8/2018 | |
| KR | 10-1900065 B1 | 9/2018 | |
| KR | 10-1900066 B1 | 9/2018 | |
| KR | 10-1920617 B1 | 11/2018 | |
| KR | 10-2020-0042285 A | 4/2020 | |
| KR | 10-2020-0046458 A | 5/2020 | |
| WO | 03/053423 A2 | 7/2003 | |
| WO | 2006/055965 A2 | 5/2006 | |
| WO | 2006/055965 A3 | 5/2006 | |
| WO | 2007/061783 A1 | 5/2007 | |
| WO | 2010/095706 A1 | 8/2010 | |
| WO | 2012/135032 A2 | 10/2012 | |
| WO | 2013/170006 A2 | 11/2013 | |
| WO | 2013/170006 A3 | 11/2013 | |
| WO | 2013/170006 A4 | 11/2013 | |
| WO | 2014/110177 A2 | 7/2014 | |
| WO | 2015/009824 A1 | 1/2015 | |
| WO | 2016145159 A1 | 9/2016 | |
| WO | 2017/041094 A1 | 3/2017 | |
| WO | 2017/102703 A1 | 6/2017 | |

OTHER PUBLICATIONS

Marie Carmel Balcos et al., "Docosahexaenoic acid inhibits melanin synthesis in murine melanoma cells in vitro through increasing tyrosinase degradation", Acta Pharmacologica Sinica, 2014, pp. 489-495, vol. 35.
Office Action issued Jan. 5, 2024 in U.S. Appl. No. 17/288,109.
Office Action issued Jun. 18, 2024 in U.S. Appl. No. 17/288,109.
Priscila Saito, et al., "The Lipid Mediator Resolvin D1 Reduces the Skin Inflammation and Oxidative Stress Induced by UF Irradiation in Hairless Mice", Front. Pharmacol., 2018, vol. 9, Article 1242 pp. 1-15.
Juntao Xu, et al., "Resolvin D1 attenuates imiquimod-induced mice psoriasiform dermatitis through MAPKs and NF-kB pathways", Journal of Dermatological Science, Feb. 2018, pp. 127-135, vol. 89, Issue 2.
S Bang, et al., "17(R)-resolvin D1 specifically inhibits transient receptor potential ion channel vanilloid 3 leading to peripheral antinociception", British Journal of Pharmacology, 2012, pp. 683-692, vol. 165.
Jeremy W. Winkler, et al., "Resolvin D4 stereoassignment and its novel actions in host protection and bacterial clearance", Scientific Reports, 2016, pp. 1-11, vol. 6, document No. 18972.
Julia Homann, et al., "In Vivo Availability of Pro-Resolving Lipid Mediators in Oxazolone Induced Dermal Inflammation in the Mouse", Plos One, 2015, pp. 1-20, vol. 10, No. 11.
International Searching Authority, International Search Report for PCT/KR2019/013920 dated Feb. 21, 2020 (PCT/ISA/210).
Riyesh Menon et al., "Pro-Resolution Potency of Resolvins D1, D2 and E1 on Neutrophil Migration and in Dermal Wound Healing", Nano Life, 2017, vol. 7, No. 1, pp. 1750002-1-1750002-1 O (10 pages total).
Donald Y.M. Leung et al., "New insights into atopic dermatitis", The Journal of Clinical Investigation, 2004, vol. 113, No. 5, pp. 651-657 (8 pages total).
Office Action issued Apr. 17, 2024 in U.S. Appl. No. 17/285,214.
Office Action issued Jan. 4, 2024 in U.S. Appl. No. 17/285,214.
International Searching Authority, International Search Report of PCT/KR2019/013516 dated Jan. 28, 2020 [PCT/ISA/210].

* cited by examiner

METHOD FOR WHITENING SKIN USING COMPOSITION FOR SKIN WHITENING

CROSS-REFERENCE TO RELATED APPLICATION

This application claims priority to and the benefit of Korean Patent Application No. 10-2021-0067754 filed in the Korean Intellectual Property Office on May 26, 2021, the entire contents of which are incorporated herein by reference.

BACKGROUND OF THE INVENTION

(a) Field of the Invention

This disclosure relates to a method for whitening a skin using a whitening composition.

(b) Description of the Related Art

A skin performs various functions essential for the human body to survive. Barrier functions to maintain homeostasis inside the human body in response to environmental changes, sensory functions to recognize external changes, and body temperature control functions are among the most representative skin functions. Among the various functions of the skin, in particular, the barrier functions of the skin are mainly manifested by the stratum corneum at the outermost portion of the skin. Since the stratum corneum has been reported to affect functions, roles, structures, and the like of an inner living cell layer, that is, an epidermal layer or a dermal layer, as well as performs the simple barrier functions, its importance is constantly increasing. This stratum corneum is composed of dead keratinocytes and intercellular lipids, and plays a key function as a skin protective layer that protects the skin from external stimuli and prevents moisture from evaporating from the inside. In addition, the keratinocytes in the stratum corneum create a skin barrier through differentiation and keratinization processes.

There are various factors that cause aging in human skin. In particular, ultraviolet (UV) rays cause wrinkles, a decrease in elasticity, pigmentation, and a decrease in a skin moisture content due to damage on the skin barrier. When the skin surface moisture content decreases due to skin damage caused by the ultraviolet rays, the stratum corneum on the skin surface loses flexibility and thus makes the skin dry, eventually failing in properly functioning as a barrier. Therefore, in order to enhance the skin barrier, it is very important to maintain moisturizing power of the skin.

There are two types of pores that are related to water homeostasis existing in the epidermis, namely aquaporins (AQP) and tight junctions (TJ). In addition, filagrin is a precursor protein of natural moisturizing factor (NMF) responsible for moisturizing the skin, and it is known that the ability to promote filagrin production plays an important role in moisturizing.

On the other hand, various inflammatory dermatitises are caused by IgE-related immune mechanisms, and there are many reports that a delayed immune response caused by T-cell abnormalities is involved therein. In particular, around a skin area where atopic dermatitis has occurred, invasion of immune-related cells such as macrophages, Th lymphocytes, and mast cells is greatly increased. Patients with atopic dermatitis show a high IgE concentration in the blood, because the number of Th2 cells increases, these Th2 cells secrete Th2 cytokines such as IL-4, IL-13, and the like, which stimulate B lymphocytes, and IgE secretion is stimulated through stimulation of the B lymphocytes. In particular, in case of early atomic dermatitis, IL-4 and IL-13 play an important role.

In treatment and prevention of inflammation such as the atopic dermatitis, it is very important to make an inflammation-resolving mediator actively involved. The inflammation-resolving mediator in actively involved in inflammation resolution, and is naturally produced and secreted from immune cells (neutrophil, macrophage) in the tissues at the end of an inflammatory reaction. The inflammation-resolving mediator has various forms such as lipids, proteins, and gas molecules, and particularly, a pro-resolving lipid mediator (specialized pro-resolving lipid mediators, SPMs) among them have been actively studied in recent years. The pro-resolving lipid mediator is a metabolite produced by metabolism of eicosapentaenoic acid (EPA) or docosahexaenoic acid (DHA), which is an omega-3 polyunsaturated fatty acid (PUFA), in cells. Up to now, there have been many reports on alleviating inflammation responses by the pro-resolving lipid mediator, but it is unknown that the pro-resolving lipid mediator has an effect on melanogenesis of melanocytes and is used for enhancing skin whitening efficacy. Accordingly, the present inventors have confirmed that while developing a natural skin whitening agent which is safe for the human body, the pro-resolving lipid mediator does not only have the skin whitening efficacy in an environment without a pigmentation inducer but also suppresses the pigmentation inducer from causing a pigmentation phenomenon and furthermore, reinforces the whitening efficacy by inhibiting acne-causing bacteria (*Cutibacterium acnes, C. acnes*) from inducing the melanogenesis and thus, completing one aspect of the present disclosure.

SUMMARY OF THE INVENTION

An embodiment provides a cosmetic composition capable of improving skin hyper-pigmentation.

Another embodiment provides a method for whitening a skin of a subject, including administering the cosmetic composition to the subject.

According to an embodiment, a whitening composition includes a compound including a structural unit represented by Chemical Formula A and including at least one hydroxyl group and at least one carboxyl group as an active ingredient.

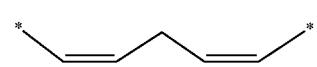

[Chemical Formula A]

The compound included as the active ingredient may include a compound represented by Chemical Formula 1.

[Chemical Formula 1]

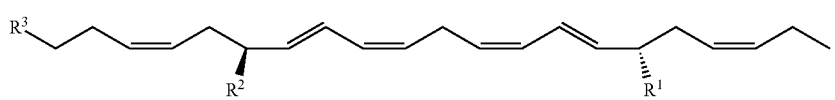

In Chemical Formula 1, $R^1$ to $R^3$ are each independently a hydrogen atom, a hydroxyl group, or a carboxyl group, wherein at least one of $R^1$ to $R^3$ is a hydroxyl group, and at least one of $R^1$ to $R^3$ is a carboxyl group.

$R^1$ and $R^2$ may be each independently a hydroxyl group, and $R^3$ may be a carboxyl group.

The compound represented by Formula 1 may be included at a concentration of about 0.001 nM to about 1 μM based on the total amount of the composition.

The compound represented by Formula 1 may be included at a concentration of about 0.01 nM to about 100 nM based on the total amount of the composition.

The compound included as the active ingredient may include a compound represented by Chemical Formula 2.

The compound included as the active ingredient may include a compound represented by Chemical Formula 3.

The concentration of the compound represented by Chemical Formula A and including at least one hydroxyl group and at least one carboxyl group may be the same as described above, and the composition may include the compounds represented by Chemical Formula 1 to Chemical Formula 3, which is also the same as described above.

The composition according to an embodiment not only inhibits the increase in protein expression of melanin-producing enzymes (TRP1, TRP2, tyrosinase) in melanocytes by *C. acnes*, but also even when skin pigmentation occurs irrespective of acne-causing bacteria, by inhibiting the increase in protein expression of melanin-producing enzymes (TRP2, tyrosinase) in melanocytes, an excellent whitening effect may be imparted to the skin applied with the composition. That is, it is confirmed that the composition according to an embodiment not only has a skin whitening effect in an environment without a pigmentation inducer, but also inhibits the pigmentation phenomenon caused by the pigmentation inducer, and furthermore, it is confirmed that

[Chemical Formula 2]

[Chemical Formula 3]

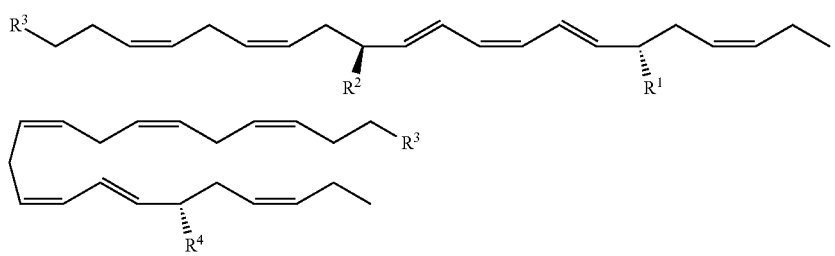

In Chemical Formula 2, $R^1$ to $R^3$ are each independently a hydrogen atom, a hydroxyl group or a carboxyl group, wherein at least one of $R^1$ to $R^3$ is a hydroxyl group, and at least one of $R^1$ to $R^3$ is a carboxyl group, and in Chemical Formula 3, $R^3$ and $R^4$ are each independently a hydroxyl group or a carboxyl group, wherein at least one of $R^3$ and $R^4$ is a hydroxyl group, and at least one of $R^3$ and $R^4$ is a carboxyl group.

The whitening composition may be a cosmetic composition.

According to another embodiment, a method for whitening a skin of a subject includes administering a cosmetic composition including the compound including the structural unit represented by Chemical Formula A and including at least one hydroxyl group and at least one carboxyl group as an active ingredient, to the subject.

According to another embodiment, a use of the compound represented by Chemical Formula A and including at least one hydroxyl group and at least one carboxyl group for the preparation of a whitening composition is provided.

According to another embodiment, a method of whitening the skin by applying a composition including an effective amount of the compound represented by Chemical Formula A (including at least one hydroxyl group and at least one carboxyl group), to the skin.

by inhibiting the induction of melanin production by acne-causing bacteria (*Cutibacterium acnes, C. acnes*) is inhibited to impart an excellent whitening effect to the skin coated with the composition.

DETAILED DESCRIPTION OF THE EMBODIMENTS

Figure 1:
FIGS. 1 to 3 are photographs and graphs each independently showing that the composition according to an embodiment inhibits an increase in protein expression of melanin-producing enzymes (TRP2, tyrosinase) in normal human melanocytes.
Figure 1:
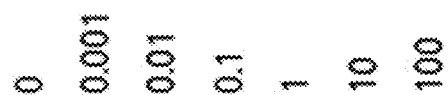

Hereinafter, exemplary embodiments of the present disclosure will be described in detail, and may be easily performed by a person having ordinary skill in the related art. However, this disclosure may be embodied in many different forms, and is not to be construed as limited to the exemplary embodiments set forth herein.

In the present specification, improvement of a skin whitening function means that a color of a stratum corneum located on the outside of the skin is changed to bright and white. The stratum corneum, which is a primary barrier of the skin, may be easily damaged by an external environment. In general, an external preparation may be prescribed in order to impart whitening power to the skin, which is a temporary solution but not a fundamental solution to the problem, and furthermore, since the external preparation rather solves most of problems but has an effect of just covering black marks on the skin, the pigmentation problem of the skin has not been fundamentally improved through the prescription of simply applying the external preparation to the skin.

Accordingly, the present inventors have confirmed that a compound represented by a specific chemical formula, which constitutes a composition according to an embodiment, solves the fundamental problem and thus fundamentally improve skin whitening efficacy, completing one aspect of the present disclosure.

Specifically, the composition according to an embodiment regulates a signaling mechanism in relation to expression of melanin-producing enzymes (TRP1, TRP2, tyrosinase) involved in melanin synthesis, from which skin whitening effects may be expected.

In this regard, the fact has been found that when an intracellular concentration of c-AMP increases, melanogenesis increases, and when an extracellular signal regulated kinase (ERK) pathway is activated, the melanogenesis is reduced. However, as a method of activating the extracellular signal regulated kinase pathway, a method of stimulating signaling pathways that phosphorylate the extracellular signal regulated kinase is well known, and in recent years, when a protein phosphatase 2A (PP2A), an enzyme that dephosphorylates the extracellular signal regulated kinase, is inhibited, the extracellular signal regulated kinase is activated, which may eventually contribute to achieving the skin whitening effects due to decomposition of a microphthalmia-associated transcription factor (MITF), but a method of effectively inhibiting the protein phosphatase 2A has not been known yet.

In this regard, the present inventors have confirmed that when melanocytes are treated with a composition including a specific compound as an active ingredient (specifically, a composition including the specific compound as an active ingredient within a particular concentration range), there are synthesis inhibitory effects of the melanin-producing enzymes (TRP1, TRP2, tyrosinase), completing one aspect of the present disclosure.

On the other hand, in the conventional methods, substances directly inhibiting the melanin-producing enzymes (TRP1, TRP2, tyrosinase) should be used at a high concentration and may not only exhibit side effects such as skin irritation and the like, but also kojic acid has been banned because of the potential to cause skin cancer. However, the composition according to an embodiment is not a substance directly inhibiting the melanin-producing enzymes (TRP1, TRP2, tyrosinase) and thus may not only irritate the skin and have almost no side effects but also exhibit much stronger whitening effects through inhibition of production of the melanin-producing enzymes (TRP1, TRP2, tyrosinase).

In the present specification, it will be understood that when an element such as a layer, film, region, or substrate is referred to as being "on" another element, it may be directly on the other element or intervening elements may also be present. In contrast, when an element is referred to as being "directly on" another element, there are no intervening elements present.

As used herein, when specific definition is not otherwise provided, "combination" refers to mixing or copolymerization. In addition, "copolymerization" refers to block copolymerization or random copolymerization, and "copolymer" refers to a block copolymer or a random copolymer.

Hereinafter, a composition for skin whitening according to an embodiment is described.

A composition for skin whitening according to an embodiment includes a compound including a structural unit represented by Chemical Formula A and including at least one hydroxyl group and at least one carboxyl group as an active ingredient.

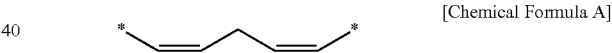

[Chemical Formula A]

For example, the compound included as the active ingredient may include a compound represented by Chemical Formula 1.

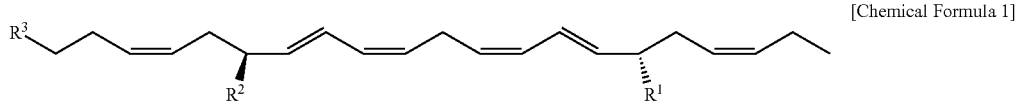

[Chemical Formula 1]

In Chemical Formula 1, $R^1$ to $R^3$ are each independently a hydrogen atom, a hydroxyl group, or a carboxyl group, wherein at least one of $R^1$ to $R^3$ is a hydroxyl group, and at least one of $R^1$ to $R^3$ is a carboxyl group.

For example, in Chemical Formula 1, $R^1$ and $R^2$ may each independently be a hydroxyl group, and $R^3$ may be a carboxyl group.

The compound represented by Chemical Formula 1 is one of pro-resolving lipid mediators (specialized pro-resolving lipid mediators, SPMs) and may not only inhibit acne-causing bacteria (*C. acnes*) from increasing protein expressions of the melanin-producing enzymes TRP1 and TRP2 in melanocytes but also, in skin pigmentation inducers (α-MSH, IBMX, etc.) in addition to the acne-causing bacteria (*C. acnes*), inhibit the increased protein expression of the melanin-producing enzyme (TRP2, tyrosinase) and thus impart whitening effects to the skin.

Hyperpigmentation on the skin may be caused by various factors such as hormonal abnormalities after inflammation reaction of the skin, genetic diseases, ultraviolet (UV) irradiation, and the like, and among them, abnormality in synthesis and distribution of melanin pigments and the like may be counted as main factors.

Melanin has a main function of scavenging oxygen radicals and protecting the skin from damages caused therefrom. Therefore, a lot of the melanin means an effective countermeasure system for protecting the skin from physical and chemical toxic substances. The melanin is produced by enzymatic action and spontaneous oxidation after tyrosine is converted into dopaquinone by the melanin-producing enzymes (TRP1, TRP2, tyrosinase) in melanocytes.

Methods for inhibiting the melanogenesis known up to date are largely as follows.

First, there is a method of blocking ultraviolet (UV) to remove a main cause of the melanogenesis. In this method, a light scattering agent or a light blocking agent may be included in a cosmetic composition, which brings about good results.

Next, the melanogenesis may be suppressed by inhibiting synthesis of core carbohydrates required for activity of the melanin-producing enzymes (TRP1, TRP2, tyrosinase), for example, glucosamine.

In addition, kojic acid or arbutin may be used to inhibit a function of the melanin-producing enzyme (TRP1) involved in the melanogenesis.

Furthermore, substances with specific toxicity to the melanocytes producing melanin, for example, hydroquinone may be used to interfere division of the melanocytes.

In addition, a method of reducing and decolorizing the produced melanin has been introduced.

Currently, most of research for discovering a whitening composition is focused on substances that directly inhibit the melanin-producing enzymes (TRP1, TRP2, tyrosinase) involved in the melanin synthesis. However, in addition to directly inhibiting the melanin-producing enzymes (TRP1, TRP2, tyrosinase), it has been suggested that whitening effects may be expected by regulating signal transduction involved in expressions of the melanin-producing enzymes (TRP1, TRP2, tyrosinase). (Briganti S, Camera E, Picardo M. Pigment Cell Res, 2003, 16 2:101-10)

In addition, the melanin-producing enzymes (TRP1, TRP2, tyrosinase) are known to be produced by controlling MITF (microphthalmia-associated transcription factor), which is a transcription factor, when under the influence of external stimuli or hormones (D S Kim, E S Whang, J E Lee, S Y Kim, S B Kwon, and K C Park. J Cell Sci.2003; 116:1699-706), but a method of reducing the melanogenesis by inhibiting expression of the MITF has not been introduced yet.

The composition according to an embodiment reduces the melanogenesis through the inhibition of the production of the melanin-producing enzymes (TRP1, TRP2, tyrosinase) and specifically, has an excellent effect of inhibiting an increase in protein expressions of the melanin-producing enzymes (TRP1, TRP2, tyrosinase) by acne-causing bacteria (*C. acnes*) and the like in the melanocytes and accordingly, when used on the skin where hyper-pigmentation is induced by the acne-causing bacteria (*C. acnes*) or other factors causing skin pigmentation, has very excellent skin whitening effects. For example, when the composition according to an embodiment is applied to the skin around acne, the very excellent skin whitening effects may be expected.

An embodiment provides a composition for skin whitening including the compound represented by Chemical Formula 1 as an active ingredient, wherein the composition may include a pharmaceutically effective amount of the compound represented by Chemical Formula 1 alone or at least one pharmaceutically acceptable carrier, excipient, or diluent.

The compound represented by Chemical Formula 1 may be included at a concentration of about 0.001 nM to about 1 μM, for example, about 0.01 nM to about 100 nM, for example, about 1 nM to about 100 nM based on the total amount of the composition. For example, the compound represented by Chemical Formula 1 in the composition may be included at a concentration of greater than or equal to about 0.001 nM, greater than or equal to about 0.01 nM, greater than or equal to about 0.1 nM, or greater than or equal to about 1 nM and at a concentration of less than or equal to about 1 μM or less than or equal to about 100 nM based on the total amount of the composition. When the compound represented by Chemical Formula 1 is used at a concentration of less than about 0.001 nM, since the acne-causing bacteria (*C. acnes*) or the skin pigmentation-inducing factors little inhibit the increase in protein expressions of the melanin-producing enzymes (TRP1, TRP2, tyrosinase) in melanocytes, having no effect of improving a skin whitening function. In addition, when the compound represented by Chemical Formula 1 is used at a concentration of greater than about 1 μM, cytotoxicity may occur and harm the human body, and when the compound represented by Chemical Formula 1 is used at a concentration of greater than about 100 nM, the cytotoxicity may be relatively reduced, but compared with when the compound represented by Chemical Formula 1 is included at a concentration of about 1 nM to about 100 nM, there may be no large difference in the skin whitening effects, wherein the compound represented by Chemical Formula 1 may be rather excessively included and thus limit roles and the like of other functional ingredients in the composition.

For example, the whitening composition may include a compound represented by Chemical Formula 2 as an active ingredient.

[Chemical Formula 2]

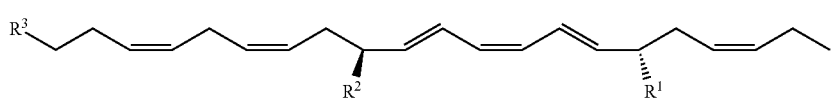

In Chemical Formula 2, $R^1$ to $R^3$ are each independently a hydrogen atom, a hydroxyl group, or a carboxyl group, wherein at least one of $R^1$ to $R^3$ is a hydroxyl group, and at least one of $R^1$ to $R^3$ is a carboxyl group.

For example, Chemical Formula 2 may be represented by Chemical Formula 2-1, but is not necessarily limited thereto.

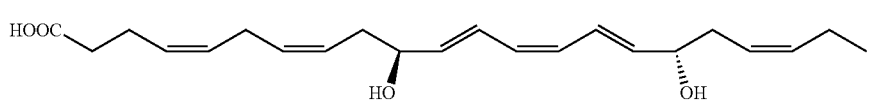

[Chemical Formula 2-1]

For example, the whitening composition may include a compound represented by Chemical Formula 3.

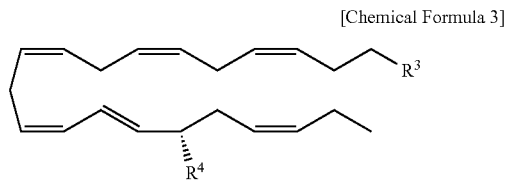

[Chemical Formula 3]

In Chemical Formula 3, $R^3$ and $R^4$ are each independently a hydroxyl group or a carboxyl group, wherein at least one of $R^3$ and $R^4$ is a hydroxyl group, and at least one of $R^3$ and $R^4$ is a carboxyl group.

For example, Chemical Formula 3 may be represented by Chemical Formula 3-1, but is not necessarily limited thereto.

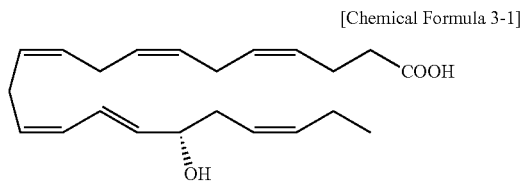 [SMILES: CC/C=C\C[C@H](O)/C=C/C=C\C/C=C\C/C=C\C/C=C\CCC(=O)O]

[Chemical Formula 3-1]

In the above, "pharmaceutically effective amount" refers to an amount sufficient to allow the physiologically active ingredient to be administered to an animal or human to exhibit desired physiological or pharmacological activity. However, the pharmaceutically effective amount may vary according to the degrees of symptoms, ages, weights, health status, sexes, administration routes, and duration of treatment.

In addition, "pharmaceutically acceptable" refers to physiologically acceptable when administered to humans, and usually does not cause allergic reactions or similar reactions, such as gastrointestinal disorders or dizziness. Examples of the carrier, excipient, and diluent may include lactose, dextrose, sucrose, sorbitol, mannitol, xylitol, erythritol, maltitol, starch, acacia rubber, alginate, gelatin, calcium phosphate, calcium silicate, cellulose, methyl cellulose, polyvinyl pyrrolidone, water, methylhydroxybenzoate, propylhydroxybenzoate, talc, magnesium stearate, and mineral oils. In addition, it may further include fillers, anticoagulants, lubricants, wetting agents, fragrances, emulsifiers, and antiseptics.

For example, the composition may be a cosmetic composition.

In the present specification "cosmetic" may refer to any material that may have a medical function in addition to the cosmetic function.

The formulation of the cosmetic composition is not particularly limited and may be appropriately selected as desired.

For example, the cosmetic composition may be formulated into formulations such as solutions, suspension liquids, emulsions, pastes, gels, creams, lotions, powders, soaps, surfactant-containing cleansings, oils, powder foundations, emulsion foundations, wax foundations, and sprays, but is not limited thereto. More specifically, it may be formulated into cosmetic compositions such as detergents, tonics, hair dressings, nourishing lotions, essences, serums, treatments, conditioners, shampoos, lotions, wools, or hair dyes, and the like, and may be formulated into basic cosmetics such as an oil-in-water (O/W) type, a water-in-oil (W/O), and the like.

For example, the composition may have a formulation selected from skin lotion, skin toner, astringent, lotion, milk lotion, moisture lotion, nourishing lotion, massage cream, nourishing cream, moisture cream, hand cream, ointment, foundation, essence, nourishing essence, pack, soap, cleansing foam, cleansing lotion, cleansing cream, body lotion, body cleanser, lotion, ointment, gel, cream, patch, or spray. In addition, in the composition, in addition to the above-mentioned essential components in each formulation, other components may be appropriately selected and formulated without difficulty by a person of ordinary skill in the art according to types or use purposes of other external preparations. For example, ultraviolet (UV) blocking agents, hair conditioning agents, fragrances, and the like may be further included.

The cosmetic composition may include a cosmetically acceptable medium or base. These are all formulations suitable for topical applications. The cosmetic composition may be provided in the form of emulsions obtained by dispersing an oil phase in an aqueous phase, suspensions, microemulsions, microcapsules, microgranules, or ion-type (liposome) and/or non-ionized vesicle dispersing agents, or in the form of creams, skins, lotions, powders, ointments, sprays, or conceal sticks. These compositions may be prepared according to conventional methods in the art.

When the formulation of one aspect of the present disclosure is a solution or emulsion, a solvent, a solubilizer, or an emulsifier may be used as carrier components. For example, water, ethanol, isopropanol, ethyl carbonate, ethyl acetate, benzyl alcohol, benzyl benzoate, propylene glycol, 1,3-butylglycol oil, glycerol aliphatic ester, polyethylene glycol, or fatty acid ester of sorbitan may be used.

If the formulation of one aspect of the present disclosure is a suspension, the carrier component may be a diluent of a liquid such as water, ethanol or propylene glycol, a suspending agent such as ethoxylated isostearyl alcohol, polyoxyethylene sorbitol ester, and polyoxyethylene sorbitan ester, microcrystalline cellulose, aluminum metahydroxide, bentonite, agar, tragacanth, and the like.

If the formulation of one aspect of the present disclosure is pastes, creams, or gels, the carrier component may be animal oil, vegetable oil, wax, paraffin, starch, tragacanth, cellulose derivatives, polyethylene glycol, silicone, bentonite, silica, talc or zinc oxide.

If the formulation of one aspect of the present disclosure is powders or sprays, the carrier component may be lactose, talc, silica, aluminum hydroxide, calcium silicate, or polyamide powders. Particularly, in the case of sprays, a propellant such as a chlorofluorohydrocarbon, propane/butane, or dimethyl ether may be additionally included.

In an embodiment of one aspect of the present disclosure, the cosmetic composition may include thickeners. The thickeners included in the cosmetic composition of one aspect of the present disclosure may be methyl cellulose, carboxyl methyl cellulose, carboxyl methyl hydroxy guanine, hydroxy methyl cellulose, hydroxyethyl cellulose, a carboxyl vinyl polymer, polyquaternium, cetearyl alcohol, stearic acid, and carrageenan, preferably one or more of carboxyl methyl cellulose, a carboxyl vinyl polymer, and polyquaternium may be used, and more preferably a carboxyl vinyl polymer may be used.

In an embodiment of one aspect of the present disclosure, the cosmetic composition may include a variety of suitable bases and additives as needed, and the types and amounts of these components may be easily selected by the inventor. If necessary, it may include an acceptable additive, and may further include for example, conventional ingredients such as antiseptics, pigments, additives, and the like.

The antiseptics may specifically be phenoxyethanol or 1,2-hexanediol, and the fragrances may be artificial fragrances.

In an embodiment of one aspect of the present disclosure, the cosmetic composition may include a composition selected from a water-soluble vitamin, an oil-soluble vitamin, a polymeric peptide, a polymeric polysaccharide, a sphingolipid, and a seaweed extract. Other ingredients that may be added include fats and oils, humectants, emollients, surfactants, organic and inorganic pigments, organic powders, ultraviolet (UV) absorbers, antiseptics, fungicides, antioxidants, plant extracts, pH adjusters, alcohols, pigments, fragrances, blood circulation accelerators, coolants, anhidrotics, purified water, and the like.

In addition, the compounding components which may be added other than these are not limited thereto. Moreover, any component may be blended in the range which does not damage the purpose and effect of the invention.

Furthermore, the cosmetic composition according to an embodiment may be used not only as a pharmaceutical composition as described above, but also as a dietary supplement. For example, it may be easily used as main ingredients, auxiliary ingredients, food ingredients, food additives, functional foods, or beverages.

The "food" means a natural or processed product including one or more nutrients, and preferably means that it is ready to be eaten directly after a certain amount of processing. It includes all foods, food additives, functional foods, and beverages.

The foods to which the food composition can be added may include, for example, various foods, beverages, gums, teas, vitamin composites, and functional foods. In addition, the foods may include special nutritional products (e.g., formulas, baby food, etc.), processed meat products, fish products, tofu, jellies, noodles (e.g. ramen noodles, etc.), breads, dietary supplements, seasoned foods (e.g., soy sauce, soybean paste, red pepper paste, mixed soy sauce, etc.), sauces, sweets (e.g. snacks), candy, chocolate, gum, ice cream, dairy products (e.g. fermented milk, cheese, etc.), other processed foods, kimchi, pickles (various kimchis, pickles, etc.), beverages (e.g., fruit beverages, vegetable beverages, soy milk, fermented beverages, etc.), natural seasonings (e.g., ramen soup, etc.), but are not limited thereto. The foods, beverages, or food additives may be prepared by conventional manufacturing methods.

In addition, "functional foods" or "health functional foods" refers to a food group that has added values to foods by using physical, biochemical, or biotechnological techniques to act and express functions of foods for specific purposes, or foods that are processed and designed to fully express the body's regulatory functions, such as defense rhythm control of food compositions, disease prevention, and recovery of living bodies. It may specifically be health functional foods. The functional foods may include acceptable food auxiliary additives and may further include suitable carriers, excipients, and diluents commonly used in the manufacture of functional foods.

The types of dietary supplements are not limited thereto, but may be in a form of powders, granules, tablets, capsules, or beverages.

Another embodiment provides a method for whitening a skin of a subject including administering the cosmetic composition to the subject the composition. The composition is the same as described above.

The administrating may be performed by a method known in the art. The administrating may be performed directly to the subject by any means, for example, by routes such as intravenous, intramuscular, oral, transdermal, mucosal, intranasal, intratracheal or subcutaneous administration. The administrating may be systemically or locally. The administrating may be topically performed to a site where skin aging is present. The administrating may be, for example, performed by application. The application refers to any method of bringing the composition into contact with the skin of an individual in an appropriate way, through which the composition may be absorbed into the skin.

The subject may be a mammal, such as a human, cow, horse, pig, dog, sheep, goat, or cat. The subject may be a subject in need of ameliorating, delaying, or inhibiting skin hyper-pigmentation. The subject may be an individual in need of inhibiting cell death, inhibiting protein expression of melanin-producing enzyme (tyrosinase), or increasing anti-oxidant activity.

In the administrating, the composition according to an embodiment may be administered in an amount of about 0.01 mg to about 10,000 mg, about 0.1 mg to about 1,000 mg, for example, about 0.1 mg to about 500 mg, about 0.1 mg to about 100 mg, about 0.1 mg to about 50 mg, about 0.1 mg to about 25 mg, about 1 mg to about 1,000 mg, about 1 mg to about 500 mg, about 1 mg to about 100 mg, about 1 mg to about 50 mg, about 1 mg to about 25 mg, about 5 mg to about 1,000 mg, about 5 mg to about 500 mg, about 5 mg to about 100 mg, about 5 mg to about 50 mg, about 5 mg to about 25 mg, about 10 mg to about 1,000 mg, about 10 mg to about 500 mg, about 10 mg to about 100 mg, about 10 mg to about 50 mg, or about 10 mg to about 25 mg per day. Or the composition according to an embodiment may be administrated so that the composition may work at a concentration (working concentration) of about 0.01 µM to about 25 µM, about 0.05 µM to about 5 µM, about 0.075 µM to about 3.75 µM, about 0.1 µM to about 2.5 µM, about 0.15 µM to about 2 µM, about 0.25 µM to about 1.5 µM, about 0.4 µM to about 1.25 µM, about 0.5 µM to about 1.2 µM, or about 0.75 µM to about 1.15 µM.

Advantages and features of one aspect of the present disclosure and methods for achieving them will be apparent with reference to the examples described in detail below. One aspect of the present disclosure will be described in detail with reference to examples. However, these examples are specifically provided for describing one aspect of the present disclosure, and the range of one aspect of the present disclosure is not limited to these examples.

EXAMPLES

Experimental Example 1: Confirmation of Inhibition of Increase in Protein Expression of Melanin-producing Enzymes (Tyrosinase, TRP2) in Normal Human Melanocytes Normal human melanocytes are placed on a 6-well plate, and the next day, the medium is changed to a melanocyte-free melanocyte medium. At this time, they are treated with each composition including the compound represented by Chemical Formula 1-1 (Cayman chemical) in an amount of 0 nM, 0.001 nM, 0.01 nM, 0.1 nM, 1 nM, 10 nM, and 100 nM, respectively (based on the total amount of the composition). After culturing for 4 days, the cells are broken using a lysis buffer in each well and then the proteins are separated. Subsequently, the separated proteins are measured with respect to relative protein expression levels by using a specific antibody for tyrosinase which is a melanin-producing enzyme from, TRP2 (tyrosinase related protein 2). As a control group, an expression level of GAPDH is checked, and the results are shown in FIGS. 1 to 3.

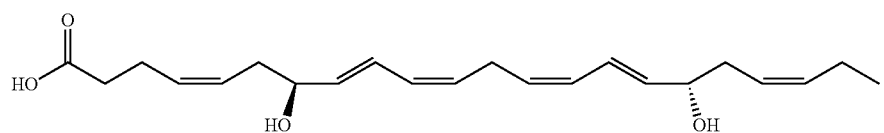

[Chemical Formula 1-1]

Figure 2:
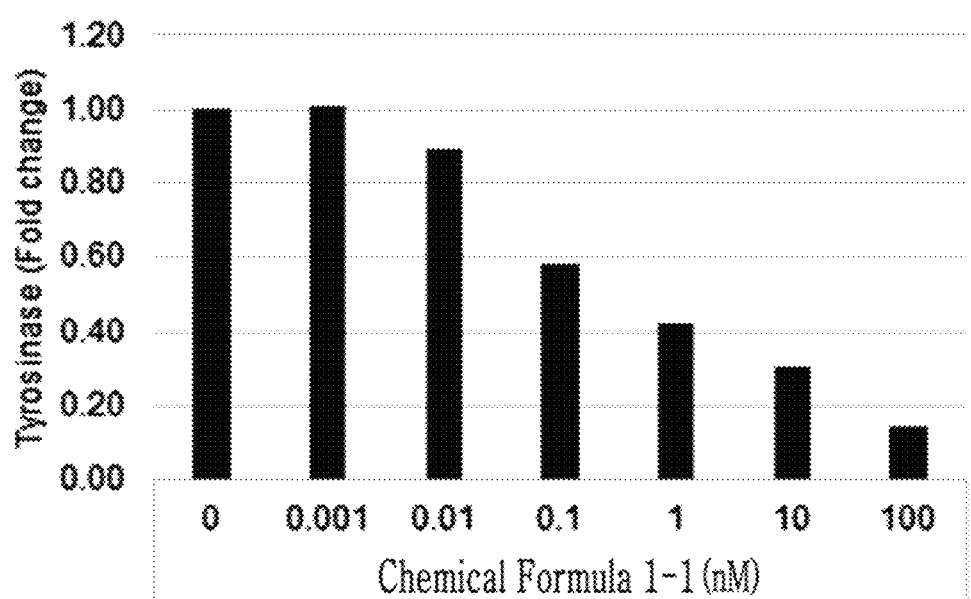
Figure 3:
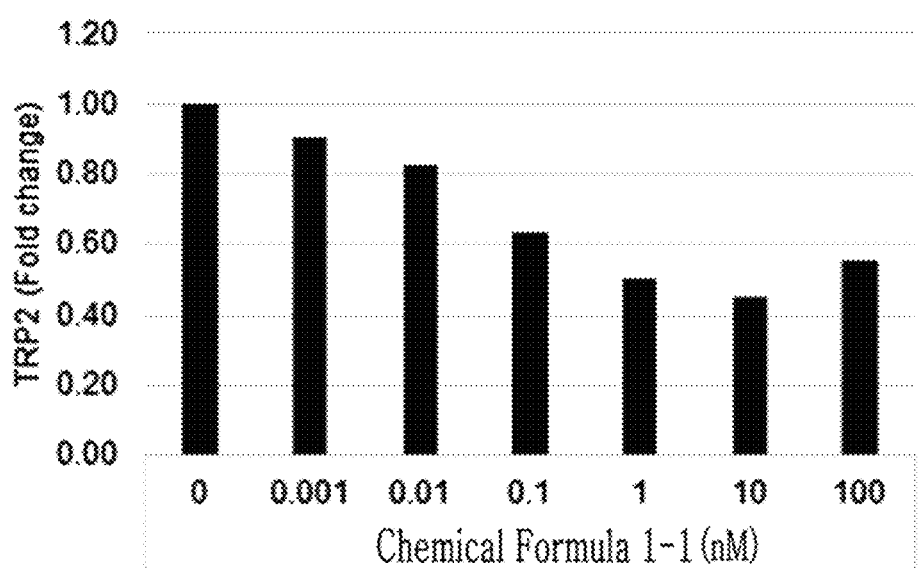

From FIGS. 1 to 3, when the compound represented by Chemical Formula 1-1 is included, an increase in the protein expression of the melanin-producing enzyme (tyrosinase, TRP2) in normal human melanocytes is effectively inhibited regardless of *C. acnes*. Particularly, an increase in protein expression of the tyrosinase is effectively inhibited depending on a concentration of the compound represented by Chemical Formula 1-1.

Experimental Example 2: Confirmation of Inhibition of Increase in Protein Expression of Melanin-producing Enzyme (Tyrosinase, TRP2) by Pigmentation Inducer (α-MSH)

Normal human melanocytes are placed on a 6-well plate, and the next day, the medium is changed to a PMA-free melanocyte medium. At this time, they are treated with each composition including the compound represented by Chemical Formula 1-1 (Cayman chemical) in an amount of 0 nM, 0.001 nM, 0.01 nM, 0.1 nM, 1 nM, 10 nM, and 100 nM, respectively (based on the total amount of the composition) along with 500 nM pigmentation inducer (α-MSH). After culturing for 4 days, the cells are broken using a lysis buffer in each well and then the proteins are separated. Subsequently, the separated proteins are measured with respect to relative protein expression levels by using a specific antibody for TRP2 (tyrosinase related protein 2), which is a melanin-producing enzyme. As a control group, an expression level of GAPDH is checked, and the results are shown in FIGS. 4 to 6.

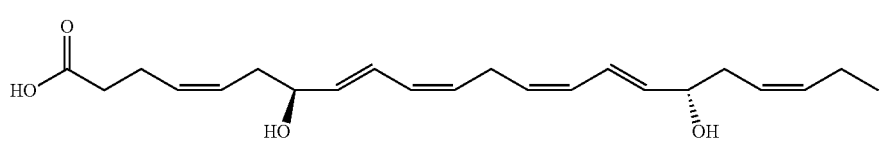

[Chemical Formula 1-1]

Figure 4:
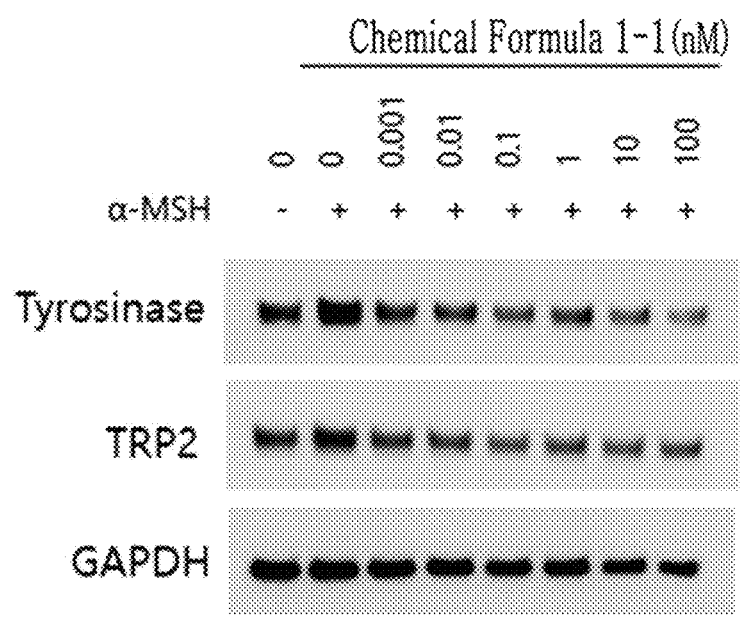
FIGS. 4 to 6 are photographs and graphs each independently showing that the composition according to an embodiment inhibits an increase in protein expression of the melanin-producing enzyme (TRP2, tyrosinase) caused by the pigmentation inducer (α-MSH), not the acne-causing bacteria (*C. acnes*).
Figure 5:
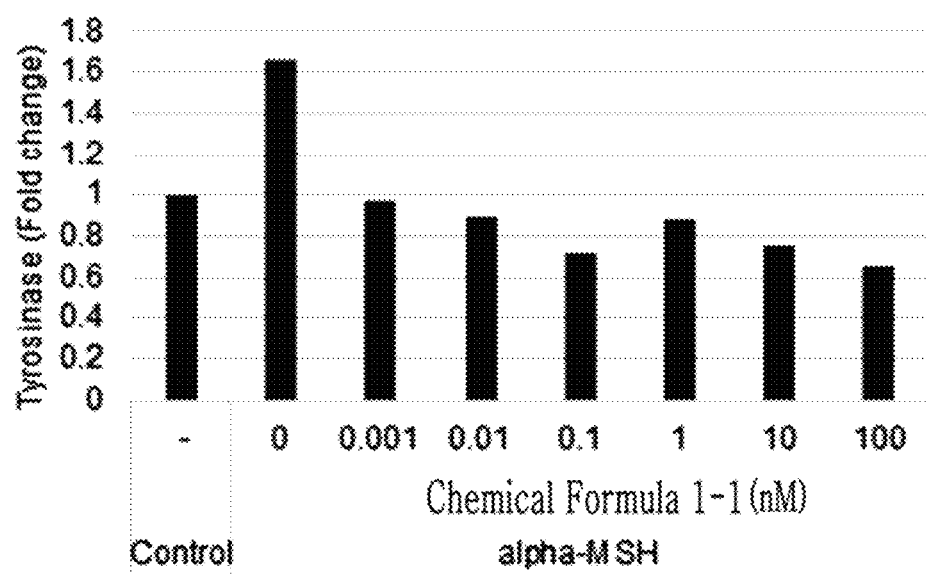
Figure 6:
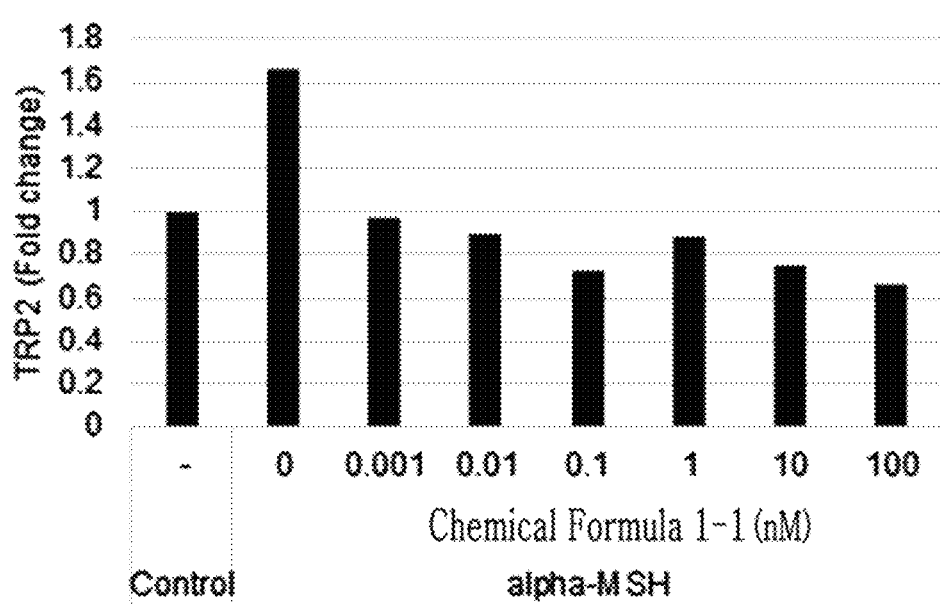

From FIGS. 4 to 6, when the compound represented by Chemical Formula 1-1 is included, an increase in protein expression of the melanin-producing enzyme (tyrosinase, TRP2) is effectively inhibited by a pigmentation inducer (α-MSH).

Experimental Example 3: Confirmation of Inhibition of Increase in Protein Expression of Melanin-producing Enzyme (Tyrosinase, TRP2) by Pigmentation Inducer (IBMX)

Figure 7:
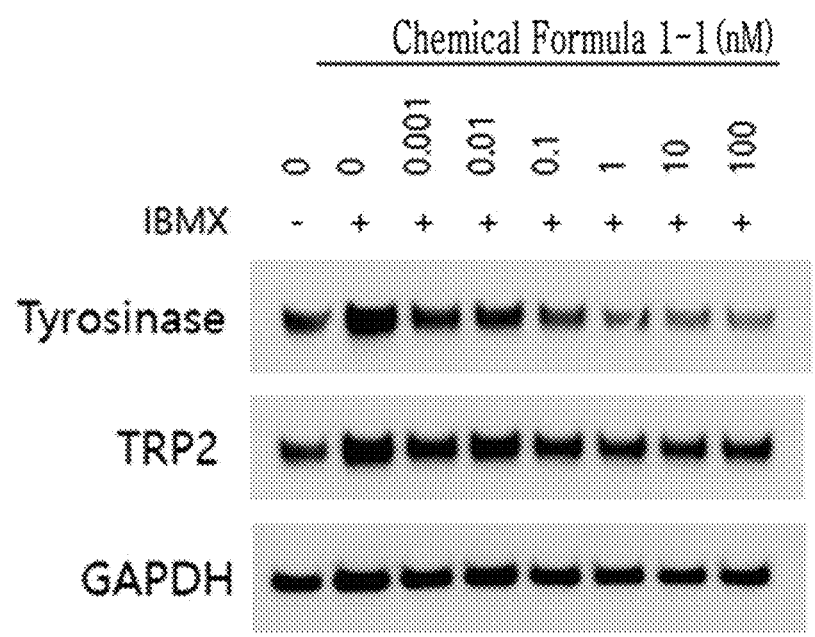
FIGS. 7 to 9 are photographs and graphs each independently showing that the composition according to an embodiment inhibits an increase in protein expression of the melanin-producing enzyme (TRP2, tyrosinase) by the pigmentation inducer (IBMX), not the acne-causing bacterium (*C. acnes*).
Figure 8:
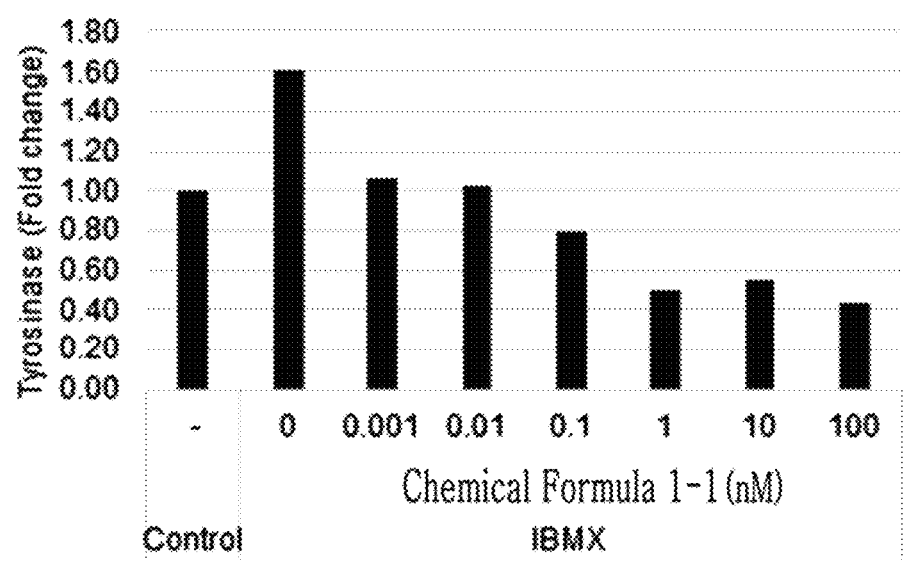
Figure 9:
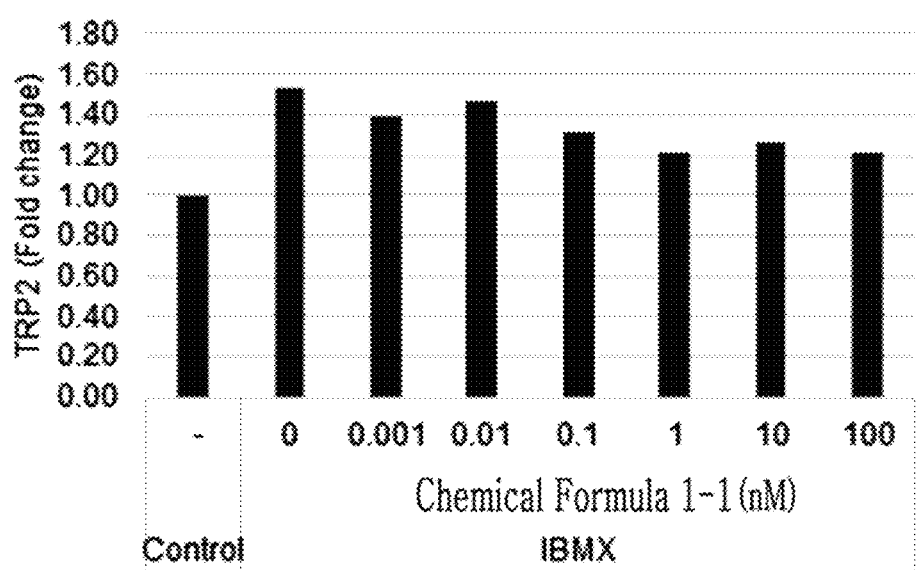

Normal human melanocytes are placed on a 6-well plate, and the next day, the medium is changed to a PMA-free melanocyte medium. At this time, they are treated with each composition including the compound represented by Chemical Formula 1-1 (Cayman chemical) in an amount of 0 nM, 0.001 nM, 0.01 nM, 0.1 nM, 1 nM, 10 nM, and 100 nM, respectively (based on the total amount of the composition) along with 100 μM pigmentation inducer (IBMX). After culturing for 4 days, the cells are broken using a lysis buffer in each well and then the proteins are separated. Subsequently, the separated proteins are measured with respect to relative protein expression levels by using a specific antibody for TRP2 (tyrosinase related protein 2), which is a melanin-producing enzyme. As a control group, an expression level of GAPDH is checked, and the results are shown in FIGS. 7 to 9.

Herein, $10^4$, $10^5$, $10^6$, and $10^7$ CFU/ml of live C. acnes are treated. After culturing for 2 days, the cells broken by using a lysis buffer in each well to separate proteins. The separated proteins are measured with respect to relative protein expression levels by using a specific antibody for TRP1 (tyrosinase related protein 1) and TRP2 (tyrosinase related protein 2), which are melanin-producing enzymes. As a control group, an expression level of GAPDH is checked, and the results are shown in FIG. 10.

Figure 10:
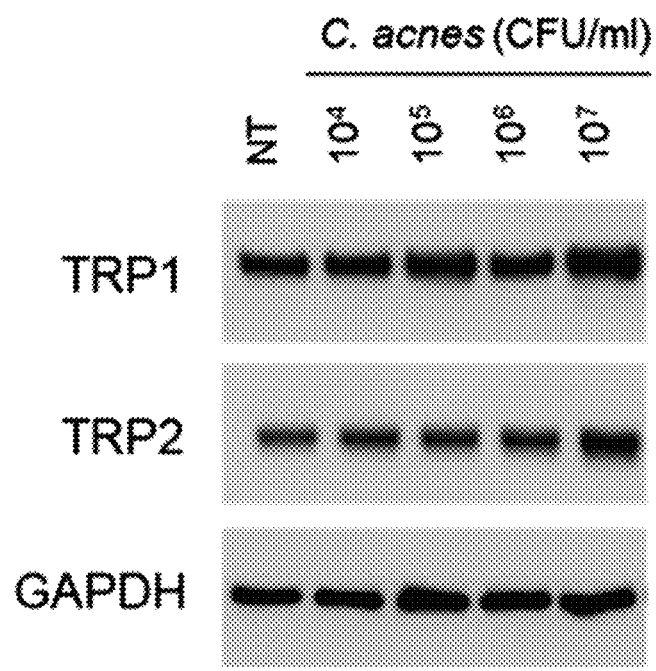
FIG. 10 is a photograph showing that acne-causing bacteria (*C. acnes*) increases the protein expression of melanin-producing enzymes (TRP1, TRP2).

Referring to FIG. 10, the acne-causing bacteria (C. acnes) turn out to increase protein expressions of the melanin-producing enzymes TRP1 and TRP2 in the melanocytes.

Experimental Example 5: Confirmation of Inhibition of Increase in Protein Expression of Melanin-producing Enzymes (TRP1, TRP2) by C. Acnes Normal human melanocytes are placed on 6-well plates, and the next day, the medium is changed to a PMA-free melanocyte medium. Herein, they are treated with each composition including the compound represented by Chemi-

[Chemical Formula 1-1]

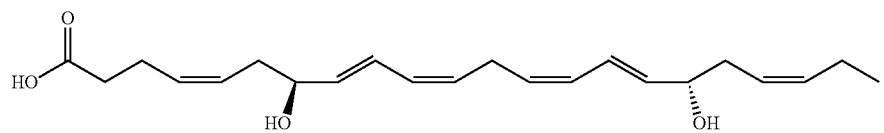

From FIGS. 7 to 9, when the compound represented by Chemical Formula 1-1 is included, an increase in protein expression of the melanin-producing enzyme (tyrosinase, TRP2) is effectively inhibited by a pigmentation inducer (IBMX).

Figure 11:
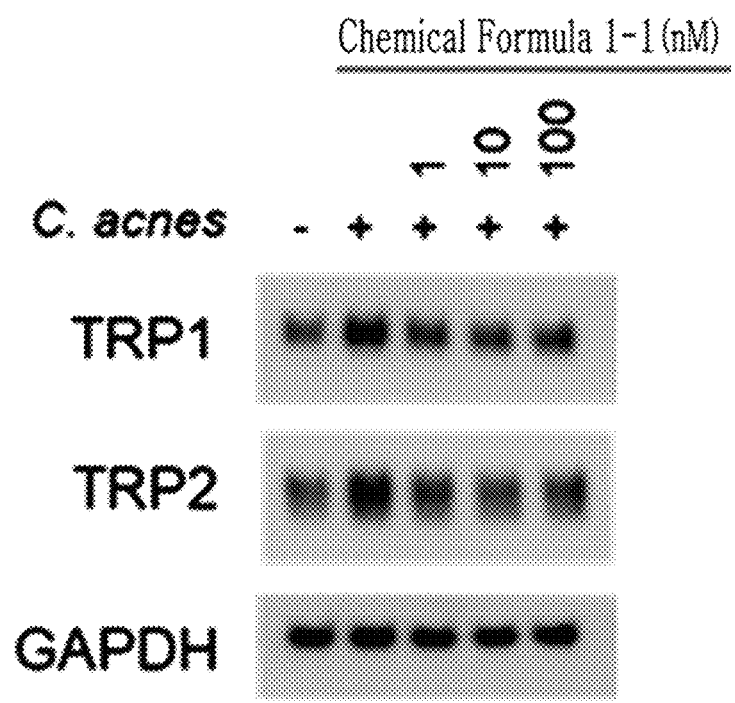
FIGS. 11 and 12 are photographs and graphs each independently showing that the composition according to an embodiment inhibits an increase in protein expression of melanin-producing enzymes (TRP1, TRP2) by acne-causing bacteria (*C. acnes*).
Figure 12:
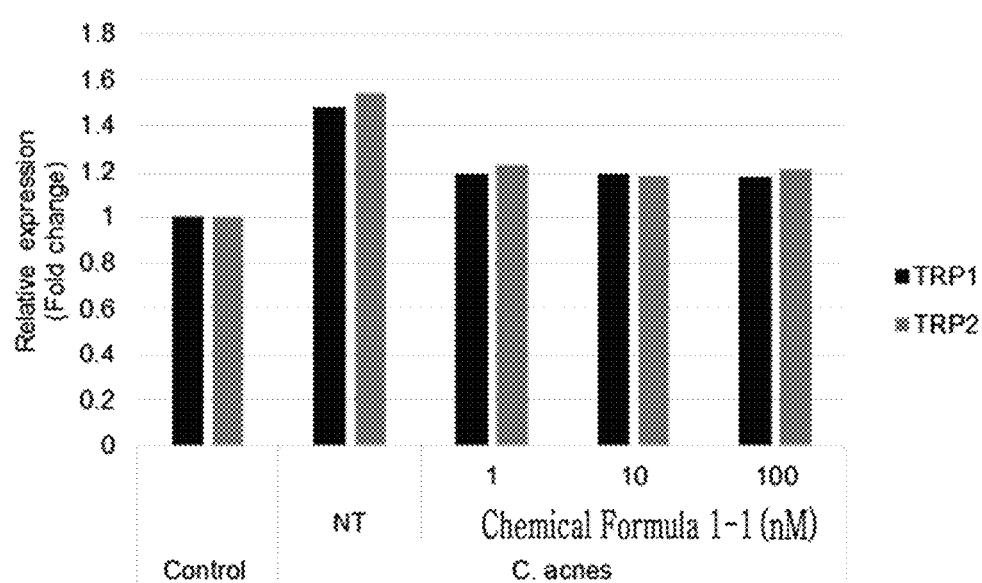

Experimental Example 4: Confirmation of Whether C. Acnes Increases Protein Expression of Melanin-producing Enzymes (TRP1, TRP2) or not Cutibacterium acnes (C. acnes, ATCC 6919) are inoculated in a BHI medium and cultured at 37° C. under cal Formula 1-1 (Cayman chemical) at 1 nM, 10 nM, and 100 nM (based on the total amount of the composition) along with $10^7$ CFU/ml of live C. acnes. After culturing for 2 days, the cells broken by using a lysis buffer in each well to separate proteins. The separated proteins are measured with respect to relative protein expression levels by using a specific antibody for TRP1 (tyrosinase related protein 1) and TRP2 (tyrosinase related protein 2), which are melanin-producing enzymes. As a control group, an expression level of GAPDH is checked, and the results are shown in FIGS. 11 and 12.

[Chemical Formula 1-1]

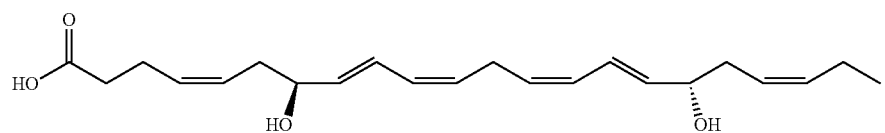

anaerobic conditions for 72 hours to 96 hours, and then, the medium is collected. The collected medium is centrifuged (4° C., 10 minutes at 5,000×g), precipitating the bacteria. The precipitated bacteria are twice washed with phosphate-buffered saline (PBS) and treated up to a final concentration of $10^{10}$ CFU/ml, preparing a live C. acnes stock, and the live C. acnes stock is cryopreserved at −80° C. Normal human melanocytes are placed on 6-well plates, and the next day, the medium is changed to a PMA-free melanocyte medium.

From FIGS. 11 and 12, when the compound represented by Chemical Formula 1-1 is included within a concentration range of 1 nM to 100 nM, an increase in protein expression of the melanin-producing enzyme (TRP1, TRP2) by C. acnes is effectively inhibited.

Although the preferred embodiments of one aspect of the present disclosure have been described in detail, the scope of one aspect of the present disclosure is not limited thereto, and various modifications and improvements by those skilled in the art using the basic concept of one aspect of the present disclosure defined in the following claims are also within the scope of the invention.

What is claimed is:

1. A method for whitening a skin of a subject in need thereof, consisting of
administering a cosmetic composition consisting of a compound of the following Chemical Formula, as a single active ingredient, and a pharmaceutically acceptable carrier, excipient, or diluent, to the skin of the subject:

Chemical Formula

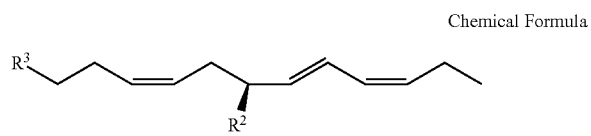
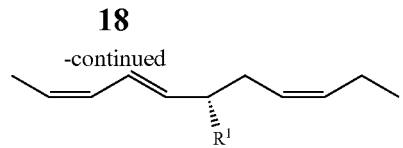

wherein, in the Chemical Formula,
$R^1$ and $R^2$ are each independently a hydroxyl group, and $R^3$ is a carboxyl group; and
wherein the compound of the Chemical Formula is included at a concentration of about 0.01 nM to about 10 nM based on a total amount of the cosmetic composition.

2. The method of claim 1, wherein the subject does not have an increased melanin production by acne-causing bacteria.

3. The method of claim 1, wherein the pharmaceutically acceptable carrier, excipient, or diluent is one or more selected from the group consisting of a thickener, a filler, an anti-coagulant, a lubricant, a wetting agent, a fragrance, an emulsifier, and an antiseptic.

* * * * *